United States Patent
Soerensen et al.

(10) Patent No.: US 9,469,831 B2
(45) Date of Patent: Oct. 18, 2016

(54) LACTOBACILLUS PLANTARUM CELLS WITH IMPROVED RESISTANCE TO HIGH CONCENTRATIONS OF ETHANOL

(75) Inventors: Kim Ib Soerensen, Farum (DK); Annette Kibenich, Hvidovre (DK); Eric Johansen, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 232 days.

(21) Appl. No.: 14/125,890

(22) PCT Filed: Jun. 14, 2012

(86) PCT No.: PCT/EP2012/061296
§ 371 (c)(1),
(2), (4) Date: Dec. 12, 2013

(87) PCT Pub. No.: WO2012/172000
PCT Pub. Date: Dec. 20, 2012

(65) Prior Publication Data
US 2014/0120210 A1   May 1, 2014

(30) Foreign Application Priority Data

Jun. 17, 2011  (EP) .................................... 11170349

(51) Int. Cl.
C12N 1/20    (2006.01)
C12G 1/022   (2006.01)
C12N 1/36    (2006.01)

(52) U.S. Cl.
CPC ............... *C12G 1/0203* (2013.01); *C12N 1/20* (2013.01); *C12N 1/36* (2013.01)

(58) Field of Classification Search
None
See application file for complete search history.

(56) References Cited

U.S. PATENT DOCUMENTS 7,112,346 B2    9/2006  Prahl et al.
7,625,745 B2   12/2009  Bou et al.
2010/0040730 A1  2/2010  Bou et al.

OTHER PUBLICATIONS

Bron, P. A., et al., "Use of the ALR Gene as a Food-Grade Selection Marker in Lactic Acid Bacteria", Applied and Environmental Microbiology, American Society for Microbiology, US, vol. 68, No. 11, Nov. 1, 2004, pp. 5663-5670.
International Application PCT/EP2012/061296, Search Report mailed Jul. 31, 2012.

*Primary Examiner* — Suzanne M Noakes
*Assistant Examiner* — Stephen Chong
(74) *Attorney, Agent, or Firm* — Foley & Lardner LLP

(57) ABSTRACT

Cycloserine resistant mutants of lactic acid bacteria characterized by having improved resistance towards ethanol. The cycloserine resistant mutants of lactic acid bacteria can e.g. be used for malolactic fermentations of wine (i.e. including sparkling wine such as Cava/champagne) having high alcohol levels.

11 Claims, 1 Drawing Sheet

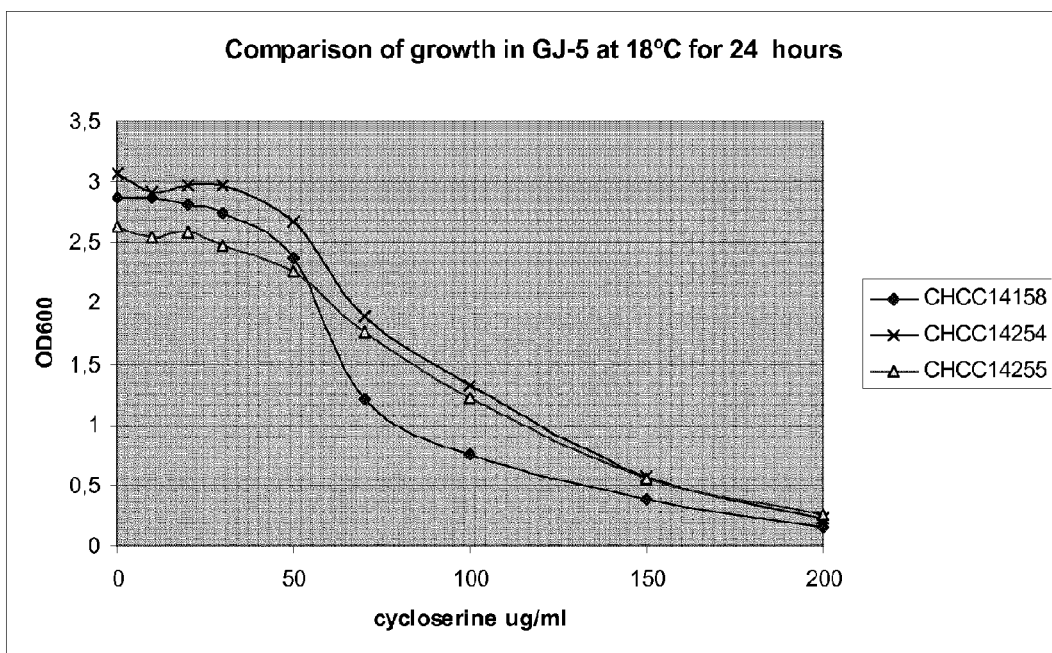

LACTOBACILLUS PLANTARUM CELLS WITH IMPROVED RESISTANCE TO HIGH CONCENTRATIONS OF ETHANOL

CROSS-REFERENCE TO RELATED APPLICATIONS

This application is a national phase of international application PCT/EP 2012/061296, filed Jun. 14, 2012, which was published on Dec. 20, 2012, as WO 2012/172000, which claims the benefit of European application No. 11170349.2, filed Jun. 17, 2011. The respective contents of each of these applications are incorporated here by reference in the entirety.

FIELD OF THE INVENTION

The present invention relates to cycloserine resistant mutants of lactic acid bacteria characterized by having improved resistance towards ethanol. The cycloserine resistant mutants of lactic acid bacteria can e.g. be used for malolactic fermentations of wine (i.e. including sparkling wine such as Cava/champagne) having high alcohol levels.

BACKGROUND ART

Lactic acid bacteria such as *Lactobacillus plantarum* and *Oenococcus oeni* are used in the wine industry for malolactic fermentation. Their functionality is based on the ability to convert malic acid into the gentler lactic acid which is used for many types of wine. Over the last decades, average temperatures have risen noticeably in the wine producing countries leading to ripened grapes with higher sugar content thereby producing wines with higher alcohol. Today many wines have an alcohol content of 14-15% and this is a substantial challenge and stress condition for the fermenting microorganism such as yeast and lactic acid bacteria.

As discussed in U.S. Pat. No. 7,625,745 B2 (Danstar Ferment, CH)—in traditional winemaking, the malolactic fermentation (MLF) is produced by means of the spontaneous growth of an indigenous flora of lactic acid bacteria. The process of MLF begins of its own accord, when the malolactic flora is sufficiently developed, that is to say in a random manner between the end of alcoholic fermentation and several weeks, even several months, after the alcoholic fermentation. When the malolactic bacteria reach a concentration of about $10^6$ CFU/ml in the medium, they enter an active metabolic phase and start the fermentation of the malic acid. In these conditions, *Oenococcus oeni* is the species most frequently responsible for the MLF. In fact, if at the start of alcoholic fermentation a predominance of the homofermentative *Lactobacillus plantarum* and *Lactobacillus casei* species is observed, these disappear when the alcohol content increases. After alcoholic fermentation, it is the species *Pediococcus* and *Oenococcus*, depending on the pH, which predominate and finally reach the critical concentration to start the MLF.

In short, one may say that natural/wildtype *Lactobacillus plantarum* strains have a relatively low inherent resistance to the concentrations of ethanol/alcohol present in the grape juice during wine production.

U.S. Pat. No. 7,625,745 B2 (PCT filed 2004 and published in 2009) describes the selection of alcohol-resistant *Lactobacillus plantarum* lactic acid bacterial strains and it is said that the authors believed that it was unexpected that it was possible to select such alcohol-resistant *Lactobacillus plantarum* lactic acid bacterial strains—e.g. due to that this resistance to alcohol was hitherto unknown for such the *Lactobacillus plantarum* strains (see e.g. C4, I. 20-30 and figures of U.S. Pat. No. 7,625,745 B2).

It is here relevant to note that in U.S. Pat. No. 7,625,745 B2 a screening was made of natural *Lactobacillus plantarum* strains arising from fermented wines (see e.g. Example 1 of U.S. Pat. No. 7,625,745 B2).

The isolates of natural lactic acid bacteria were subjected to a selection pressure of resistance to alcohol levels above 10% and two particular *L. plantarum* strains were found to be sufficiently resistant to alcohol levels above 10% (see e.g. Example 7 of U.S. Pat. No. 7,625,745 B2).

D-cycloserine (D-4-amino-isoxazolidone) is an antibiotic which inhibits alanine racemase, D-alanyl-D-alanine ligase, D-alanylalanine synthase and D-alanine permease causing cell lysis.

D-alanine racemase is essential for the production of D-alanine, an integral part of the peptidoglycan layer of the cell wall.

Strains of *Lactobacillus plantarum* in which the alanine racemase gene (air) of *Lactococcus lactis* has been inserted on a plasmid have resistance to D-cycloserine (Bron et al., 2002 Appl Environ Microbiol. 68:5663-5670).

It is here relevant to note that above discussed article of Bron et al does not in any way relate to identification of *Lactobacillus plantarum* strains with improved resistance to high concentrations of ethanol.

To the knowledge of the present inventors—there is in the prior art not described or suggested any herein relevant link between increased resistance to D-cycloserine and improved resistance to high concentrations of ethanol.

SUMMARY OF THE INVENTION

The problem to be solved by the present invention is to provide a *Lactobacillus plantarum* composition with improved resistance towards for wine relatively high concentrations of ethanol.

The *Lactobacillus plantarum* composition is particularly useful for production of wine.

The solution is based on that the present inventors have developed a novel selection method for the identification of new improved *Lactobacillus plantarum* compositions.

A novel important step of the herein described new selection method relates to that the present inventors have identified a herein surprisingly relevant link between increased resistance to D-cycloserine and improved resistance to high concentrations of ethanol.

Accordingly, the herein described novel selection method may overall be seen as comprising following two steps:
  (i): first to screen/select for *Lactobacillus plantarum* strains/cells with increased resistance to D-cycloserine—one may term it a resistance to D-cycloserine that are significantly higher than normally present in natural/wildtype *Lactobacillus plantarum* strains; and
  (ii): from the pool of D-cycloserine resistant cells identified in step (i) is then screened/selected for a *Lactobacillus plantarum* strain/cell that has improved resistance to a for wine relatively high concentrations of ethanol.

As shown in working Example 3 herein—the present inventors identified that from a pool of D-cycloserine resistant selected *Lactobacillus plantarum* strains/cells (i.e. from step (i) above) was it relatively rapid to then screen/select for a *Lactobacillus plantarum* strain/cell that has improved resistance to relatively high concentrations of ethanol—essentially, the reason for this is that the presents inventors surprisingly identified that a relatively high percentage of the first selected D-cycloserine resistant cells were also resistant to relatively high concentrations of ethanol.

Accordingly, the first screening/selection for increased D-cycloserine resistance may, as discussed herein, be seen as a kind of pre-step to rapidly and efficient be able to screen/select/enrich for a *Lactobacillus plantarum* strain/cell that has improved resistance ethanol.

As evident to the skilled person—a significant advantage of the herein described screening/selection method is that one relatively rapidly and efficiently is able to screen/select for a *Lactobacillus plantarum* strain/cell that has improved resistance ethanol.

For instance, if one already has a *Lactobacillus plantarum* strain with commercial relevant good properties in relation to e.g. malolactic fermentation of wine grape juice—one can then use this strain as a starting cell for mutagenesis and then relatively rapidly select for and thereby get/identify a novel *Lactobacillus plantarum* strain that has improved resistance to ethanol and still maintains its earlier good properties with respect to e.g. malolactic fermentation of wine grape juice.

As shown in working Example 3 herein—approximately 10% of the first selected D-cycloserine resistant cells were also resistance to relatively high concentrations of ethanol.

To the contrary—as shown in working Example 4 herein—by trying to identify an ethanol resistant cell directly from a pool of individual *Lactobacillus plantarum* mutant cells, where there had not been made the pre-step of selecting for D-cycloserine resistance, it was not even possible to identify a single ethanol resistant cell.

Accordingly, without using the novel screening/selection method as described herein—it would not (or would take a very long time) be possible to identify an ethanol resistant mutant strain of the *Lactobacillus plantarum* CHCC14158 starting strain used in working Example 3 herein.

Without being limited to theory—a theoretical explanation for the herein surprisingly identified and discussed link between increased D-cycloserine resistance and increased ethanol resistance could be that such increased D-cycloserine resistant *Lactobacillus plantarum* cells produce more of the so-called extracellular polysaccharides (EPS). It could then theoretically be that such extracellular polysaccharides (also termed exopolysaccharides) could give a kind of protection around the cell—i.e. that it could be these extracellular polysaccharides that protect the cells against D-cycloserine entry into the cells and thereby give the increased D-cycloserine resistance.

Similar and without being limited to theory—it could then also be these exopolysaccharides that would protect the *Lactobacillus plantarum* cells in high ethanol environment and thereby give the increased ethanol resistance.

As discussed above, the herein identified *Lactobacillus plantarum* cells are first selected for increased resistance to D-cycloserine—one may term it as resistance to D-cycloserine that is significantly higher than normally present in natural/wildtype *Lactobacillus plantarum* strains.

In the prior art document U.S. Pat. No. 7,625,745 B2 as discussed above—there was not made any herein relevant selection for increased resistance to D-cycloserine.

Accordingly, as understood by the skilled person—there is absolutely no reason to believe that any of the *Lactobacillus plantarum* strains described in U.S. Pat. No. 7,625,745 B2 would have a resistance to D-cycloserine as discussed herein (see e.g. working Example 1 herein, where there is described the herein relevant D-cycloserine resistance assay).

Similar, in other above discussed Bron et al., 2002 article—there was not made any herein relevant selection for increased ethanol resistance.

Accordingly, as understood by the skilled person—there is absolutely no reason to believe that any of the *Lactobacillus plantarum* strains described in the Bron et al., 2002 article would have an ethanol resistance as discussed herein (see e.g. working Example 2 herein, where there is described the herein relevant ethanol resistance assay).

In summary, it is submitted that the herein relevant discussed *Lactobacillus plantarum* strains are as such novel strains over the prior art.

Accordingly, a first aspect of the invention relates to a *Lactobacillus plantarum* composition, which comprises from $10^4$ to $10^{14}$ CFU/g *Lactobacillus plantarum* cells, wherein the *Lactobacillus plantarum* composition is characterized by that:

(i): the *Lactobacillus plantarum* cells have an increased resistance to D-cycloserine—defined by that the cells are *Lactobacillus plantarum* cells, wherein the amount of D-cycloserine that reduces the $OD_{600}$ measured growth, after 24 hours growth at 18° C., with 50% in the known Grape Juice GJ-5 medium (GJ-5 medium has the following composition: Grape juice concentrate 70.0 g, Yeast paste 30.0 g. Tween 80 0.5 g, MnSO4H2O 0.1 g and Tap water 900.0 g) as compared to the growth in the GJ-5 medium without D-cycloserine (i.e. with 0 µg/ml D-cycloserine) is higher than 70 µg/ml D-cycloserine;
and (ii): *Lactobacillus plantarum* cells have an improved resistance towards ethanol—defined by that the cells are *Lactobacillus plantarum* cells, wherein the cells can grow to an $OD_{600}$ of at least 0.8 after 3 days incubation at 25° C. in the GJ-5 medium with 11% ethanol.

As understood by the skilled person in the present context—the *Lactobacillus plantarum* composition of the first aspect herein is a composition, wherein (i): the cells (in point (i) of first aspect) are positively resistant to D-cycloserine in the D-cycloserine resistance assay of example 1; and (ii): the cells (in point (ii) of first aspect) are positively resistant to ethanol in the ethanol resistance assay of example 2.

Both the D-cycloserine resistance assay [of point (i)] and ethanol resistance assay [of point (ii)] are based on known, commercially available standard elements (such as e.g. standard media etc).

Accordingly, based on the detailed assay description herein (see e.g. example 1 herein for D-cycloserine resistance assay and example 2 herein for ethanol resistance assay) the skilled person is routinely able to repeat these assays to objectively determine whether a specific *Lactobacillus plantarum* cell of interest complies with the D-cycloserine resistance [of point (i)] and ethanol resistance [of point (ii)] levels of the first aspect of the invention.

The novel *Lactobacillus plantarum* composition as described herein may preferably be used for wine production. The dose and administration may be done according to the art.

Further, all other herein relevant steps for making a wine may be done according to the art. Such other wine production relevant steps (e.g. use of yeast cells) are well known routine steps for the skilled person and therefore not necessary to discuss in details herein.

Accordingly, a second aspect of the invention relates to a method for producing a wine comprising administering the *Lactobacillus plantarum* composition of first aspect and herein described related embodiments to a grape juice or wine and performing further adequate steps to make the wine.

A third aspect of the invention relates to a method for screening and isolating a novel *Lactobacillus plantarum* cell comprising the following steps:

(a): selecting and isolating from a pool of individual *Lactobacillus plantarum* cells, a new selected pool of *Lactobacillus plantarum* cells that have increased resistance to D-cycloserine under the conditions of point (i) of first aspect;

(b): selecting and isolating—from the selected pool of *Lactobacillus plantarum* D-cycloserine resistant cells of step (a)—a new isolated *Lactobacillus plantarum* cell that has improved resistance towards ethanol under the conditions of point (ii) of first aspect.

It is evident to the skilled person that once the inventors herein have disclosed the relevant test assays (i.e. the assays of Examples 1 and 2 herein) it will be routine work for the skilled person to select other new *Lactobacillus plantarum* cells complying with the criteria of the first aspect herein.

As discussed herein, by using the novel screening/selection method as described herein the inventors have selected and isolated a number of new improved *Lactobacillus plantarum* cells.

Embodiment of the present invention is described below, by way of examples only.

DEFINITIONS

All definitions of herein relevant terms are in accordance of what would be understood by the skilled person in relation to the herein relevant technical context.

The term "*Lactobacillus plantarum*" is a well know term to the skilled person and the skilled person knows if a particular lactic acid bacterium cell of interest is a *Lactobacillus plantarum* cell or not.

DRAWINGS

FIG. 1: In this figure the resistance to D-cycloserine of different *Lactobacillus plantarum* strains is shown: For further details—see working Examples herein.

DETAILED DESCRIPTION OF THE INVENTION

*Lactobacillus plantarum* Composition:

The term "*Lactobacillus plantarum* composition" shall be understood according to the art. It is herein understood as a *Lactobacillus plantarum* composition comprising a number of *Lactobacillus plantarum* cells with a characteristic of interest.

The *Lactobacillus plantarum* composition may comprise different types or strains of *Lactobacillus plantarum* cells (e.g. the two different *Lactobacillus plantarum* CHCC14254 and CHCC14255 strains discussed herein). In essence the composition shall simply comprise the amount of *Lactobacillus plantarum* cells given in the first aspect herein, wherein the *Lactobacillus plantarum* cells comply with the criteria given in the first aspect.

As known to the skilled person, herein commercially relevant *Lactobacillus plantarum* cell compositions are generally made by fermentation. The obtained *Lactobacillus plantarum* cells are generally concentrated, dried, mixed with a carrier and packed into a suitable container.

The relevant e.g. $10^4$ to $10^{14}$ CFU/g *Lactobacillus plantarum* cells of the composition may be present in a commercially relevant form known to the skilled person.

Accordingly, in an embodiment $10^4$ to $10^{14}$ CFU/g *Lactobacillus plantarum* cells of the composition are present as dried (e.g. spray dried) cells or as frozen cells.

In a preferred embodiment the *Lactobacillus plantarum* composition comprises from $10^6$ to $10^{14}$ CFU/g *Lactobacillus plantarum* cells, more preferably from $10^8$ to $10^{14}$ CFU/g *Lactobacillus plantarum* cells.

The term "CFU/g" relates to the gram weight of the composition as such, including suitable relevant additives present in the composition. It does not include the weight of a suitable container used to package the *Lactobacillus plantarum* composition.

An embodiment relates to that the *Lactobacillus plantarum* composition is packaged into a suitable container.

As known to the skilled person a commercially relevant bacterial composition generally also comprises other relevant suitable additives.

Beside the herein relevant *Lactobacillus plantarum* cells the composition may also comprise other relevant microorganisms of interest such as e.g. other lactic acid bacteria of interest or yeast cells of interest (such as e.g. wine yeast cells of interest).

Assay to Select for an Increased Resistance to D-cycloserine

As discussed above the D-cycloserine resistance assay of point (i) of first aspect is based on known commercially available standard elements (such as e.g. standard media, etc).

Accordingly, based on the detailed assay description herein (see e.g. example 1 herein) the skilled person is routinely able to repeat this assay to objectively determine whether a specific cell of interest complies with the D-cycloserine resistance criteria as described in point (i).

As discussed above—one may say that the level of resistance as required in the assay of example 1 is a resistance to D-cycloserine that is significantly higher than normally present in natural/wildtype *Lactobacillus plantarum* strains.

The detailed conditions of example 1 herein is herein a preferred assay to determine if a *Lactobacillus plantarum* cell of interest complies with the criteria of point (i) of first aspect.

Increased Resistance to D-cycloserine—Point (i) of First Aspect

It may be preferred that the increased resistance to D-cycloserine is higher than the one given in point (i) of the first aspect herein.

Accordingly, it may be preferred that the *Lactobacillus plantarum* cells have an increased resistance to D-cycloserine—defined by that the cells are *Lactobacillus plantarum* cells, wherein the amount of D-cycloserine that reduces the $OD_{600}$ measured growth, after 24 hours growth at 18° C., with 50% in the known Grape Juice GJ-5 medium as compared to the growth in the GJ-5 medium without D-cycloserine (i.e. with 0 µg/ml D-cycloserine) is higher than 80 µg/ml D-cycloserine or is higher than 90 µg/ml D-cycloserine.

Assay to Select for an Improved Resistance Towards Ethanol

As discussed above the ethanol resistance assay of point (ii) of first aspect is based on known commercially available standard elements (such as e.g. standard media, etc).

Accordingly, based on the detailed assay description herein (see e.g. example 2 herein) the skilled person is routinely able to repeat this assay to objectively determine whether a specific cell of interest complies with the ethanol resistance criteria as described in point (ii).

The detailed conditions of example 2 herein is herein a preferred assay to determine if a *Lactobacillus plantarum* cell of interest complies with the criteria of point (ii) of first aspect.

Improved Resistance Towards Ethanol—Point (ii) of First Aspect

It may be preferred that the improved resistance towards ethanol is higher than the one given in point (ii) of the first aspect herein.

Accordingly, it may be preferred that the *Lactobacillus plantarum* cells have an improved resistance towards ethanol—defined by that the cells are *Lactobacillus plantarum* cells, wherein the cells can grow to an $OD_{600}$ of at least 0.8 after 3 days incubation at 25° C. in the GJ-5 medium with 11.5% ethanol or with 12% ethanol or with 13% ethanol.

A Method for Producing a Wine

As said above a second aspect of the invention relates to a method for producing a wine comprising administering the *Lactobacillus plantarum* composition of first aspect and herein described related embodiments to a grape juice or wine and performing further adequate steps to make the wine.

The wine may be any wine of interest such as red wine, white wine or sparkling wine such as Cava/champagne.

As know to the skilled person—for commercial relevant wine production there is generally administrated around *Lactobacillus plantarum* cells $10^6$ CFU per ml grape juice or wine.

Accordingly, in a preferred embodiment of the method of the second aspect of the invention—there is administrated from $10^4$ CFU to $10^8$ CFU *Lactobacillus plantarum* cells per ml grape juice or wine, more preferably there is administrated from $10^5$ CFU to $10^7$ CFU *Lactobacillus plantarum* cells per ml grape juice or wine.

A Method for Cocoa Bean Fermentation

As known in the art—*Lactobacillus plantarum* cells have been used for cocoa bean fermentation.

In line of this—a herein relevant use of the *Lactobacillus plantarum* cells as described herein is use for cocoa bean fermentation—i.e. a method for cocoa bean fermentation, wherein a *Lactobacillus plantarum* composition as described herein is inoculated to the cocoa bean and then fermented.

A Method for Silage Production

As known in the art—*Lactobacillus plantarum* cells have been used for silage production.

In line of this—a herein relevant use of the *Lactobacillus plantarum* cells as described herein is use for silage production—i.e. a method for silage production, wherein a *Lactobacillus plantarum* composition as described herein is inoculated to the silage and then fermented.

A Method for Screening and Isolating a Novel *Lactobacillus plantarum* Cell

As said above, the third aspect relates to a method for screening and isolating a novel *Lactobacillus plantarum* cell.

In the method of the third aspect, a *Lactobacillus plantarum* cell capable of fulfilling the conditions of point (i) and (ii) of the first aspect is selected for.

As understood by the skilled person, the specific herein detailed described D-cycloserine resistance and ethanol resistance assays (see e.g. example 1 herein for D-cycloserine resistance assay and example 2 herein for ethanol resistance assay) parameters may be changed to make a alternative screening method that still obtains the main goals as described herein, i.e. a *Lactobacillus plantarum* cell that is capable of fulfilling the conditions of point (i) and (ii) of the first aspect.

Without being limited to theory—it could maybe be possible to use a functionally equivalent antibiotic to D-cycloserine as a selective agent to get the increased resistance to D-cycloserine of point (i) of the first aspect.

In the present context, the term "functionally equivalent antibiotic" should be understood as an antibiotic with the same mode of action or the same target as D-cycloserine, such as e.g. other inhibitors of D-alanyl-D-alanine ligases, such as e.g. vancomycin and other inhibitors of D-alanine racemase, such as e.g. O-carbamoyl-D-serine, alaphosphin and the haloalanines.

For instance, without being limited to theory—it could maybe be possible to use the functionally equivalent antibiotic vancomycin as the selective pressure agent and thereby get selected strains that are vancomycin resistant and then maybe also resistant to D-cycloserine as discussed herein (i.e. a *Lactobacillus plantarum* cell that is capable of fulfilling the conditions of point (i) of the first aspect).

As evident to the skilled person—the end result of step (b) is the isolation of a novel *Lactobacillus plantarum* that is capable of fulfilling the conditions of point (i) and (ii) of the first aspect.

Accordingly, a separate aspect of the invention relates to a *Lactobacillus plantarum* cell, which is capable of fulfilling the conditions of point (i) and (ii) of the first aspect and is obtainable by the screening method of the third aspect herein.

It is evident that this novel *Lactobacillus plantarum* cell of this separate aspect can be used to make a *Lactobacillus plantarum* composition of the first aspect.

Step (a) of the method for screening and isolating a novel *Lactobacillus plantarum* cell of the third aspect reads "selecting and isolating from a pool of individual *Lactobacillus plantarum* cells".

As known—it is routine work for the skilled person to make/create such a pool of individual *Lactobacillus plantarum* cells.

It may e.g. be made from a suitable preferred starting cell, which may be subjected to suitable mutagenesis (e.g. using a chemical mutagen or UV mutagenesis) to make a pool of mutants of said starting cell—i.e. to create a pool of individual *Lactobacillus plantarum* cells.

As discussed in working Example 3 herein—the starting *Lactobacillus plantarum* cell CHCC14158 was subjected to mutagenesis (using D-cycloserine as selective agent) and from the created pool of individual *Lactobacillus plantarum* cells was subsequently selected the novel ethanol resistant cells CHCC14254 and CHCC14255 according to the selection method as described herein.

Alternatively, one could e.g. start from cells already made to have herein relevant resistance to D-cycloserine—such as e.g. *Lactobacillus plantarum* cells described in the article of Bron et al. (2002) as discussed above.

Relevant *Lactobacillus plantarum* cells of the Bron et al. (2002) could then e.g. be subjected to a suitable mutagenesis and then selected for improved resistance towards ethanol as discussed herein.

EXAMPLES

Example 1

Cycloserine Resistance Selection Assay

Medium: The medium is the known Grape Juice GJ-5 medium described in column 20, lines 10 to 20 of U.S. Pat. No. 7,112,346 (Chr. Hansen A/S).

As described in lines 10 to 20 of U.S. Pat. No. 7,112,346—the GJ-5 medium has the following composition:
Grape juice concentrate 70.0 g
Yeast paste 30.0 g
Tween 80 0.5 g
$MnSO_4H_2O$ 0.1 g
Tap water 900.0 g As known to the skilled person—this GJ-5 medium is a medium that is considered to be representative for a grape juice used for wine production.

Further, as understood by the skilled person in the present context—a grape juice concentrate is a standard well known ingredient of such a medium.

In the present context and as understood by the skilled person—the specific Grape juice concentrate may be supplied from different suppliers and independently of the specific supplier one will (within standard measurement uncertainty) get the same herein relevant result of cycloserine resistance for a herein relevant cell of interest.

A Lactobacillus plantarum strain of interest is inoculated into 10 ml GJ-5 medium containing one of the following amounts of D-cycloserine: 0 μg/ml, 10 μg/ml, 20 μg/ml, 30 μg/ml, 50 μg/ml, 70 μg/ml, 100 μg/ml, 150 μg/ml or 200 μg/ml of D-cycloserine. The strain is grown 24 hours at 18° C. in the GJ-5 medium with the different concentrations of D-cycloserine.

After the 24 hours growth is $OD_{600}$ measured for all samples.

A Lactobacillus plantarum cell that has an increased resistance to D-cycloserine as discussed herein—is herein defined as a Lactobacillus plantarum cell, wherein the amount of D-cycloserine that reduces the $OD_{600}$ measured growth, after 24 hours growth at 18° C., with 50% in GJ-5 medium as compared to the growth in GJ-5 medium without D-cycloserine (i.e. with 0 μg/ml D-cycloserine) is higher than 70 μg/ml D-cycloserine.

Cells that are capable of complying with this increased resistance to D-cycloserine criteria are herein defined as cells that are positively resistant to D-cycloserine in the D-cycloserine resistance assay of this example 1.

Conclusion:

Based on the Cycloserine resistance Selection assay of this Example 1—for a specific strain of interest (e.g. one from a relevant commercial product)—the skilled person can routinely test if this specific strain of interest has the herein relevant Cycloserine resistance.

Example 2

Ethanol Screening Resistance Assay

Medium: The medium is the standard GJ-5 medium as used in Example 1 above.

A Lactobacillus plantarum cell that has an improved resistance towards ethanol as discussed herein—is herein defined as a Lactobacillus plantarum cell that can grow to an $OD_{600}$ of at least 0.8 after 3 days incubation at 25° C. in the GJ-5 medium with 11% ethanol.

Cells that are capable of complying with this improved resistance towards ethanol criteria are herein defined as cells that are positively resistant to ethanol in the ethanol resistance assay of this example 2.

Conclusion:

Based on the Ethanol resistance assay of this Example 2—for a specific strain of interest (e.g. one from a relevant commercial product)—the skilled person can routinely test if this specific strain of interest has the herein relevant Ethanol resistance.

Example 3

Use of D-cycloserine to Isolate Mutants of Lactobacillus plantarum with Improved Resistance to High Concentrations of Ethanol Strains
Lactobacillus plantarum CHCC14158
Lactobacillus plantarum CHCC14255 (D-cycloserine mutant of CHCC14158 isolated at 18° C. in GJ-5)
Lactobacillus plantarum CHCC14254 (D-cycloserine mutant of CHCC14158 isolated at 18° C. in GJ-5)

Mutant Isolation

Measured according to Example 1 above—Lactobacillus plantarum CHCC14158 is a cell, wherein the amount of D-cycloserine that reduces the $OD_{600}$ measured growth with 50% in GJ-5 medium as compared to the growth in GJ-5 medium without D-cycloserine (i.e. with 0 μg/ml D-cycloserine) is lower than 70 μg/ml D-cycloserine, since the amount of D-cycloserine that reduced the growth with 50% was around 60 to 65 μg/ml D-cycloserine—see e.g. FIG. 1 herein.

Accordingly, Lactobacillus plantarum CHCC14158 is not positively having increased resistance to D-cycloserine as defined in Example 1 above.

Lactobacillus plantarum strain CHCC14158 was subjected to D-cycloserine pressure as described below. The D-cycloserine worked here as a selective agent to create a pool of mutant cells with increased resistance to D-cycloserine.

In order to isolate mutants of the Lactobacillus plantarum strain CHCC14158, cells derived from the growth of a single colony were inoculated into GJ-5 medium of Example 1 containing various concentrations of D-cycloserine in the range of 25-100 μg/ml D-cycloserine and grown to saturation at 18° C. or at 25° C.

Surviving cells were diluted and plated on GJ-5 plates (without D-cycloserine) and colonies were screened in microtiter plates for the ability to grow in the presence of various concentrations of D-cycloserine in the range of 25-100 μg/ml D-cycloserine in GJ-5 medium.

25% of the resulting colonies were identified as fast growers in the presence of D-cycloserine—i.e. they were positively resistant to D-cycloserine in the D-cycloserine resistance assay of example 1.

These mutants were chosen for further study. The selected D-cycloserine resistant mutants were further purified and tested for their ability to grow in GJ-5 added various concentrations of ethanol in the range 5-14% ethanol or wine at 18° C. and 25° C. During this screening it was observed that approximately 10% of the mutants were more resistant to high concentrations of ethanol.

Two mutant derivatives of CHCC14158, designated CHCC14255 and CHCC14254, were significantly more resistant to high concentrations of ethanol than the mother strain when the growth was compared in GJ-5 at 25° C. in the presence of 11, 12 and 13 ethanol of parental strain CHCC14158 and two cycloserine resistant mutants CHCC14255 and CHCC14254.

The two cycloserine resistant mutants CHCC14255 and CHCC14254 could both grow to an $OD_{600}$ of at least 0.8 after 3 days incubation at 25° C. in the GJ-5 medium with 11% ethanol—for CHCC14255 the $OD_{600}$ was more than 1—i.e. both strains were positively resistant to ethanol in the ethanol resistance assay of this example 2.

The starting CHCC14158 strain could only grow to an $OD_{600}$ of around 0.65—i.e. the starting CHCC14158 strain was not positively resistant to ethanol in the ethanol resistance assay of this example 2.

The cycloserine resistance of both the CHCC14255 and CHCC14254 mutants was tested according to Example 1 above and both positively had the required increased resistance to D-cycloserine as required in Example 1.

For CHCC14255 the amount of D-cycloserine that reduces the $OD_{600}$ measured growth with 50% in GJ-5 medium as compared to the growth rate in GJ-5 medium without D-cycloserine (i.e. with 0 µg/ml D-cycloserine) was around 100 µg/ml D-cycloserine (see FIG. 1 herein).

For CHCC14254 the amount of D-cycloserine that reduces the $OD_{600}$ measured growth with 50% in GJ-5 medium as compared to the growth in GJ-5 medium without D-cycloserine (i.e. with 0 µg/ml D-cycloserine) was around 100 µg/ml D-cycloserine (see FIG. 1 herein).

Example 4

Reference/Control Experiment

UV mutagenesis was done on a *Lactobacillus plantarum* strain CHCC12396.

It is a strain with similar properties to *Lactobacillus plantarum* strain CHCC14158 that was used a starting cell in Example 3 above.

Screening for ethanol was done as in Example 3 above—however, after analysis of more than 100 different mutants/colonies it was not possible to select a mutant with improved resistance towards ethanol as defined in Example 2 above.

REFERENCES

1: U.S. Pat. No. 7,625,745 B2 (Danstar Ferment, CH)
2: Bron et al., 2002 Appl Environ Microbiol. 68:5663-5670
3: U.S. Pat. No. 7,112,346 (Chr. Hansen A/S)

The invention claimed is:

1. A method for producing a wine, comprising administering to a grape juice or wine a *Lactobacillus plantarum* composition comprising from $10^4$ to $10^{14}$ CFU/g *Lactobacillus plantarum* cells, wherein the *Lactobacillus plantarum* cells:
   (i) have a resistance to D-cycloserine, such that the amount of D-cycloserine required to reduce the $OD_{600}$ measured growth of the *Lactobacillus plantarum* cells by 50% after 24 hours growth at 18° C. in Grape Juice GJ-5 medium as compared to growth in Grape Juice GJ-5 medium without added D-cycloserine is higher than 70 µg/ml D-cycloserine; and
   (ii) wherein the D-cycloserine resistant *Lactobacillus plantarum* cells have a resistance towards ethanol, such that the cells can grow to an $OD_{600}$ of at least 0.8 after 3 days incubation at 25° C. in Grape Juice GJ-5 medium with 11% ethanol.

2. The method of claim 1, wherein the wine is selected from the group consisting of red wine, white wine and sparkling wine.

3. The method of claim 1, wherein the administered composition comprises from $10^4$ CFU to $10^8$ CFU *Lactobacillus plantarum* cells per ml grape juice or wine.

4. The method of claim 1, wherein the the *Lactobacillus plantarum* cells have a resistance to D-cycloserine, such that the amount of D-cycloserine required to reduce the $OD_{600}$ measured growth of the *Lactobacillus plantarum* cells by 50% after 24 hours growth at 18° C. in Grape Juice GJ-5 medium as compared to growth in Grape Juice GJ-5 medium without added D-cycloserine is higher than 80µg/ml D-cycloserine.

5. The method of claim 1, wherein the the *Lactobacillus plantarum* cells have a resistance to D-cycloserine, such that the amount of D-cycloserine required to reduce the $OD_{600}$ measured growth of the *Lactobacillus plantarum* cells by 50% after 24 hours growth at 18° C. in Grape Juice GJ-5 medium as compared to growth in Grape Juice GJ-5 medium without added D-cycloserine is higher than 90 µg/ml D-cycloserine.

6. The method of claim 1, wherein the *Lactobacillus plantarum* cells have a resistance towards ethanol, such that the cells can grow to an $OD_{600}$ of at least 0.8 after 3 days incubation at 25° C. in Grape Juice GJ-5 medium with 12% ethanol.

7. The method of claim 1, wherein the *Lactobacillus plantarum* cells have a resistance towards ethanol, such that the cells can grow to an $OD_{600}$ of at least 0.8 after 3 days incubation at 25° C. in Grape Juice GJ-5 medium with 13% ethanol.

8. The method of claim 1, wherein the *Lactobacillus plantarum* composition comprises spray-dried *Lactobacillus plantarum* cells.

9. The method of claim 1, wherein the *Lactobacillus plantarum* composition comprises frozen *Lactobacillus plantarum* cells.

10. The method of claim 1, wherein the administered composition comprises from $10^5$ to $10^7$ CFU *Lactobacillus plantarum* cells per ml grape juice or wine.

11. The method of claim 1, wherein the administered composition comprises about $10^6$ CFU *Lactobacillus plantarum* cells per ml grape juice or wine.

* * * * *